United States Patent [19]

Tanaka

[11] Patent Number: 5,621,218
[45] Date of Patent: Apr. 15, 1997

[54] METHOD AND APPARATUS INSPECTING BONDING-WIRE STATUS USING A PLURALITY OF LIGHT SOURCES

[75] Inventor: Yoshiharu Tanaka, Tokyo, Japan

[73] Assignee: NEC Corporation, Tokyo, Japan

[21] Appl. No.: 463,743

[22] Filed: Jun. 5, 1995

[30] Foreign Application Priority Data

Jun. 3, 1994 [JP] Japan .................................. 6-122575

[51] Int. Cl.⁶ .............................. G01B 11/24; H01L 21/66
[52] U.S. Cl. ................................ 250/559.34; 250/559.22; 356/375; 348/126
[58] Field of Search .................... 250/559.07, 559.08, 250/559.13, 559.15, 559.19, 559.2, 559.22, 559.29, 559.34, 559.45, 559.46; 356/375, 376, 387, 237, 238; 348/87, 90, 92, 94, 95, 126, 131

[56] References Cited

U.S. PATENT DOCUMENTS

| 4,553,843 | 11/1985 | Langley et al. | 250/559.34 |
| 4,801,810 | 1/1989 | Koso | 250/559.34 |
| 4,874,956 | 10/1989 | Kato et al. | |
| 5,302,836 | 4/1994 | Siu | 250/559.34 |

FOREIGN PATENT DOCUMENTS

| 4-273006 | 9/1992 | Japan. |
| 5-175312 | 7/1993 | Japan. |

*Primary Examiner*—Edward P. Westin
*Assistant Examiner*—John R. Lee
*Attorney, Agent, or Firm*—Young & Thompson

[57] ABSTRACT

While relatively transporting a wire to be inspected and a unit including a first light source for emitting a first beam, a second light source for emitting a second beam which intersects with said first beam at a predetermined reference position, and a photodetector for detecting reflection light of said first and second beams derived from said first and second light sources respectively, a relative position between said unit and said wire is detected as a first position when said first beam is reflected from said wire. Then, while relatively moving said unit and said wire, another relative position between said unit and said wire is detected as a second position when said second beam is reflected from said wire. Then, a height of said wire from said reference position is calculated based on an interval between said first and second positions.

32 Claims, 16 Drawing Sheets

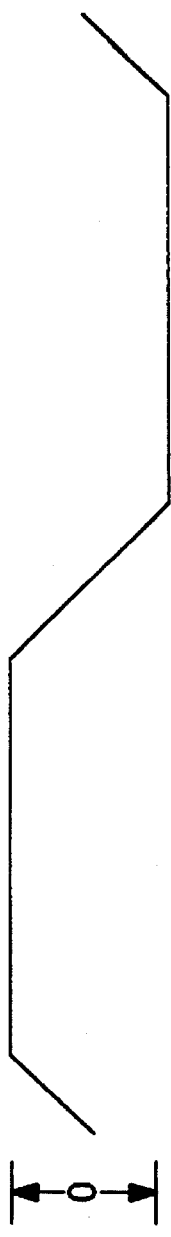
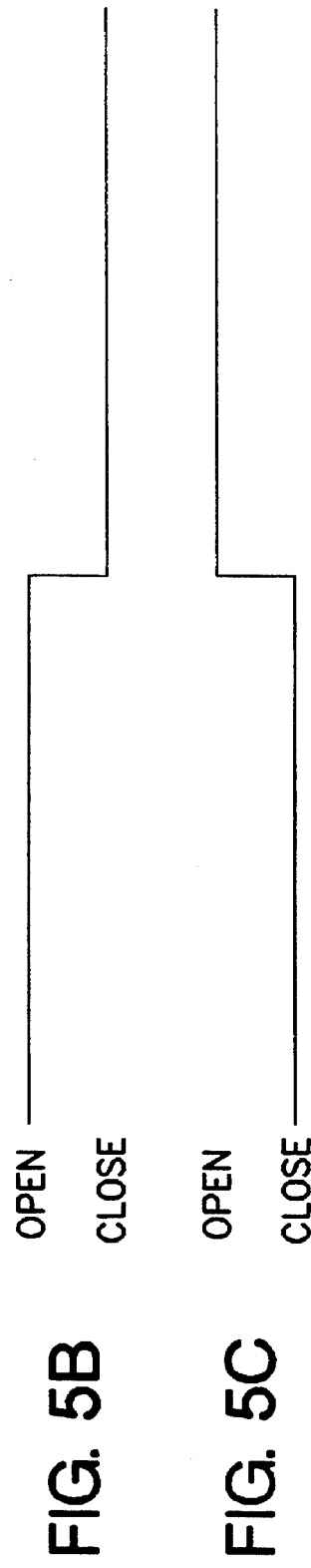
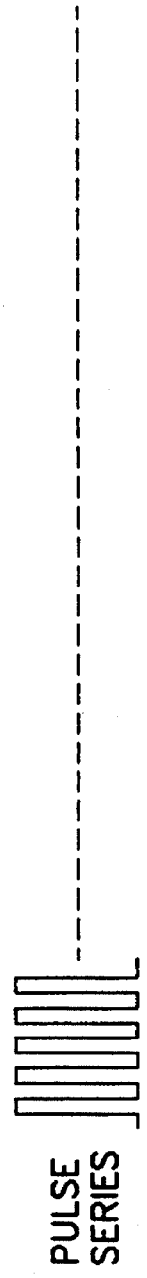
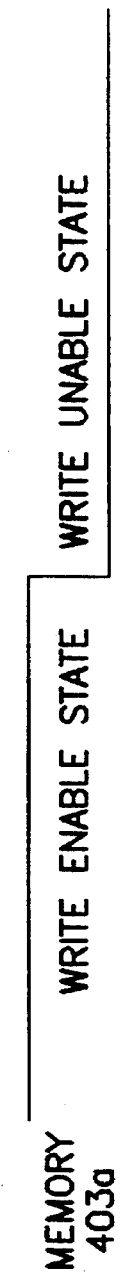

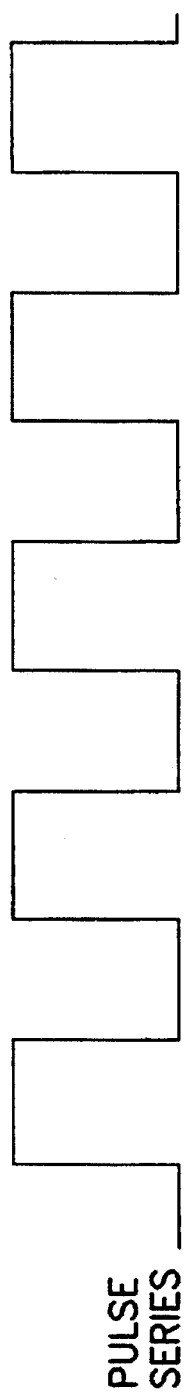
FIG. 13A PULSE SERIES
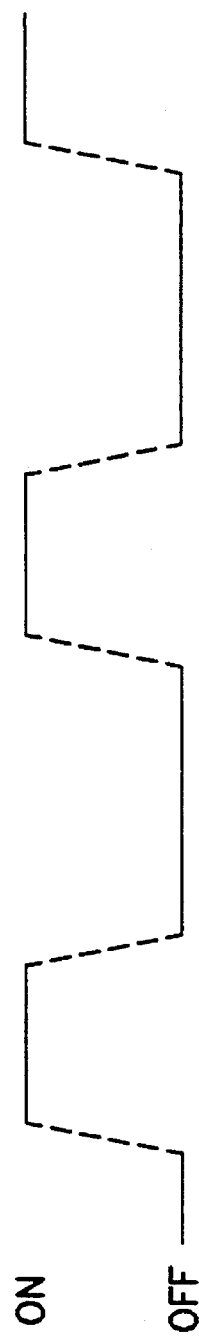
FIG. 13B ON / OFF
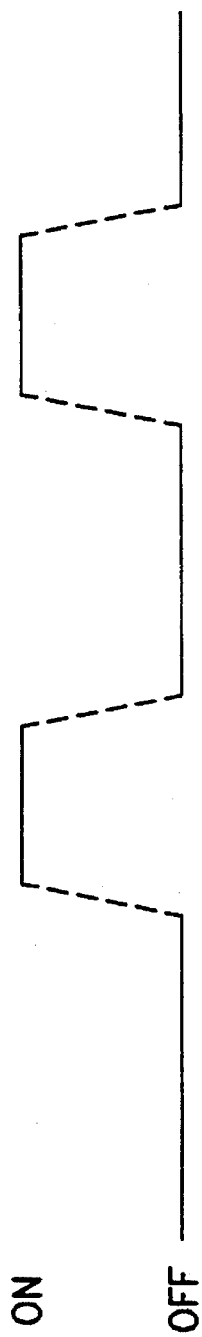
FIG. 13C ON / OFF

METHOD AND APPARATUS INSPECTING BONDING-WIRE STATUS USING A PLURALITY OF LIGHT SOURCES

BACKGROUND OF THE INVENTION

1. Field of the Invention

The present invention generally relates to a method and an apparatus for inspecting an appearance of a bonding-wire. More specifically, the present invention is directed to a method and an apparatus for inspecting an appearance of a bonding-wire connecting between a semiconductor chip and a lead frame, for instance, suitably inspecting a height shift from a preset reference plane, and also a positional shift with a horizontal plane.

2. Description of the Related Art

Recently, semiconductor packages have a large number of pins and are made thinner. Such demands are made that pitches between pins should be narrowed and longer bonding-wires are required in the wire bonding techniques for connecting semiconductor chips with lead frames. As a consequence, severe managements are necessarily required as to the loop shapes of the bonding-wires, and therefore the appearance inspection of the bonding-wire status are very important.

Conventionally, these types of bonding-wires appearance inspecting apparatuses are disclosed in, for instance, U.S. Pat. No. 4,874,956 issued on Oct. 17, 1989, Japanese Laid-Open Patent Applications Nos. Hei 4-273006 (Sep. 29, 1992) and Hei 5-175312 (Jul. 13, 1993). Then, this conventional bonding-wire appearance inspecting apparatus disclosed in Japanese Laid-open Patent Application No. Hei 5-175132 will now be described with reference to FIG. 1 and FIG. 2.

In the bonding-wire appearance inspecting apparatus shown in FIG. 1, a bonding-wire 102 is illuminated by an illumination device 101, and the reflection/scattered light from the bonding-wire 102 is imaged by an imaging device 103 mounted above the bonding-wire 102 along the vertical direction. Based on the image signal obtained from the imaging device 103, the focusing coincidence degree of the image signal is processed to obtain the numeral value by the image processing device 104. The imaging device 103 is mounted on a focus controlling device 105 to control the height. Then, while changing the height of the imaging device 103, the bonding-wire 102 is imaged to calculate the focus coincidence degree of the resulting image signal. For instance, as shown in FIG. 2, a plurality of heights F1 to F5 are preset, and the imaging device 103 is transported to image the bonding-wire 102 in such a manner that a focusing element 103a in the imaging device 103 can be focused at the respective heights F1 to F5. Then, the three-dimensional shape of the bonding-wire 102 is calculated by the central processing unit 106 based upon the focus coincidence degree calculated by the image processing device 104 and the height information of the imaging device 103 obtained from the focus control device 105. This three-dimensional shape calculation of the bonding-wire 102 is performed for all of plural bonding-wires 102 on a X-Y stage 107 by transporting the X-Y stage on which these bonding-wires, 102 are mounted. The information indicative of the calculated three-dimensional shape of this bonding-wire 102 is displayed on a display device 108.

In this conventional bonding-wire appearance inspecting apparatus, a plurality of images for the same bonding-wire must be acquired, while changing the focus positions of the imaging device 103. As a consequence, very lengthy time to input image data is required to detect the height of the bonding-wire 102. Also, since a large number of images must be processed, very complex image processing operations must be carried out.

Further, when the bonding-wire 102 is largely inclined, the reflection light from this inclined bonding-wire cannot be sufficiently detected by the imaging device 103. As a result, the appearance of the inclined bonding-wire 102 could not be inspected in high precision.

Moreover, since this conventional inspecting apparatus is equipped with no means for imaging two-dimensionally whole the semiconductor chip with the bonding-wire, the positional shift of the bonding-wire within the horizontal plane could not be inspected in high precision nor in high speed.

SUMMARY OF THE INVENTION

An object of the present invention is to provide a wire appearance inspecting method/apparatus capable of detecting a height of a wire from a reference position by way of a very simple signal process.

Another object of the present invention is to provide a wire appearance inspecting method/apparatus capable of detecting a height of a wire from a reference position in high precision even when this wire is largely inclined.

Another object of the present invention is to provide a wire appearance inspecting method/apparatus capable of detecting a height of a bonding-wire from a reference position at a high speed. This bonding-wire is bonded on pad arrays formed along the respective edges of a rectangular semiconductor chip.

A further object of the present invention is to provide a wire appearance inspecting method/apparatus capable of inspecting both of a height of a wire from a reference position and a positional shift of a wire within the horizontal plane.

To achieve the above-described objects, in accordance with a wire appearance inspecting method/apparatus of the present invention, while relatively transporting a wire to be inspected and a unit including a first light source for emitting a first beam, a second light source for emitting a second beam which intersects with the first beam at a predetermined reference position, and a photodetector for detecting reflection light of the first and second beams derived from the first and second light sources respectively, a relative position between the unit and the wire is detected as a first position when the first beam is reflected from the wire. Then, while relatively moving the unit and the wire, another relative position between the unit and the wire is detected as a second position when the second beam is reflected from the wire. Then, a height of said wire from the reference position is calculated based on an interval between the first and second positions.

As a means for achieving other objects, in a wire appearance inspecting method/apparatus of the present invention, while relatively transporting a wire and a unit including a first semiconductor laser for emitting a first beam, a second semiconductor laser for emitting a second beam which intersects with the first beam at a predetermined reference position, and a photodetector for detecting reflection light of the first and second beams derived from said first and second semiconductor lasers respectively, reflection light of said first beam and reflection light of said second beam are independently detected. The first and second beams from respective the first and second semiconductor lasers are emitted alternately for very short time. A relative transport distance between the unit and the wire which are transported since the reflection light of the first beam from the wire is detected, and until the reflection light of the second beam from the wire is detected. Then, a height of the wire from the reference position is calculated based on this transport distance.

Further, since imaging means for imaging two-dimensionally the wire is provided, both of a height of the wire from the reference position and a positional shift of the wire within the horizontal plane can precisely and speedily be inspected.

Additionally, since such a photodetector having an elongate line-shaped light receiving surface is employed which is located in a direction perpendicular to a plane formed by the first and second beams, the height of this wire from the reference position can be detected at high precision even when this wire is greatly inclined.

Instead of such a photodetector having the elongate line-shaped light receiving surface, means for condensing the reflection light of the first and second beams to the light receiving surface of the photodetector is employed, so that the same object may be achieved.

Moreover, two pairs of the first and second light sources are arranged in such a manner that the planes formed by the first and second beams is respectively located in parallel to the pad arrays formed on the perpendicular two edges of the semiconductor device. In the case, the wires corresponds to bonding-wires bonded on the respective pad arrays formed on the respective edges of the semiconductor device. As a consequence, the appearances of the bonding-wires bonded on the four edges of the semiconductor device can be easily inspected without rotating the semiconductor device.

BRIEF DESCRIPTION OF THE DRAWINGS

The present invention will be described in further detail with reference to the accompanying drawings, in which:

FIG. 5A is a timing chart showing a moving speed of a optical head;

FIG. 5B and 5C are timing charts showing opening operation and closing operation timings of shutters;

FIG. 5D is a timing chart showing a pulse series;

FIG. 5E and 5F are timing charts showing writing enable timings of memories;

FIG. 13A is a timing chart showing a pulse series;

FIG. 13B and 13C are timing charts showing driving operation timings of semiconductor lasers;

DETAILED DESCRIPTION OF THE PREFERRED EMBODIMENTS

Referring now to FIG. 3 to FIG. 11, a description will be made of an appearance inspecting apparatus for a bonding-wire, according to a first preferred embodiment of the present invention.

Figure 1:
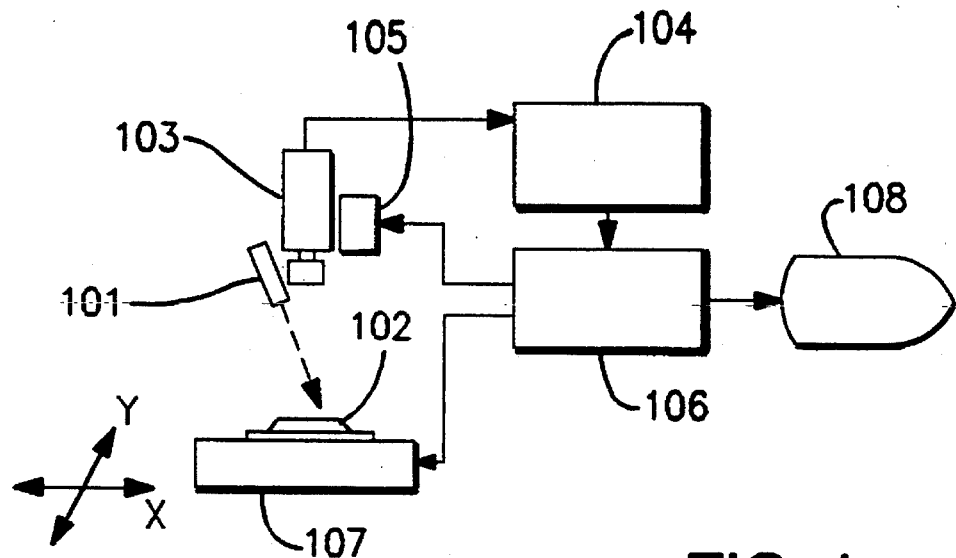
FIG. 1 is a schematic diagram showing the structure of the conventional wire appearance inspecting apparatus.
Figure 2:
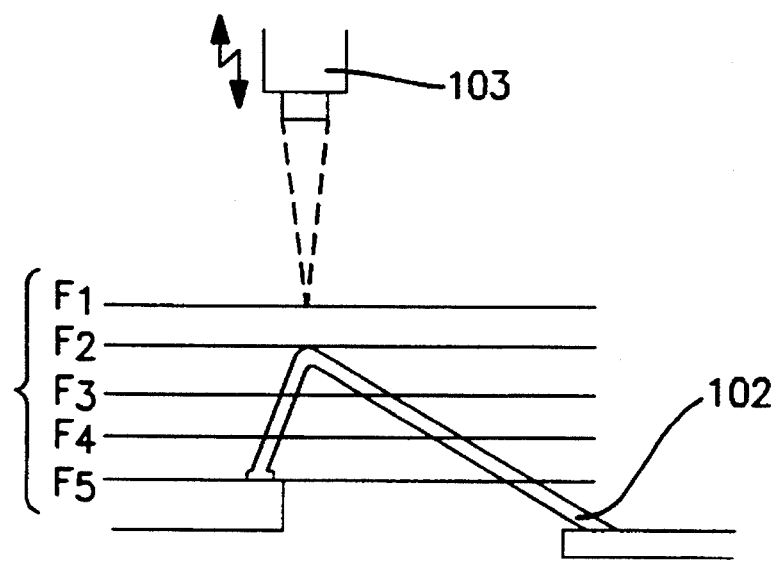
FIG. 2 is a schematic diagram for explaining the basic operation of the conventional wire appearance inspecting method.
Figure 3:
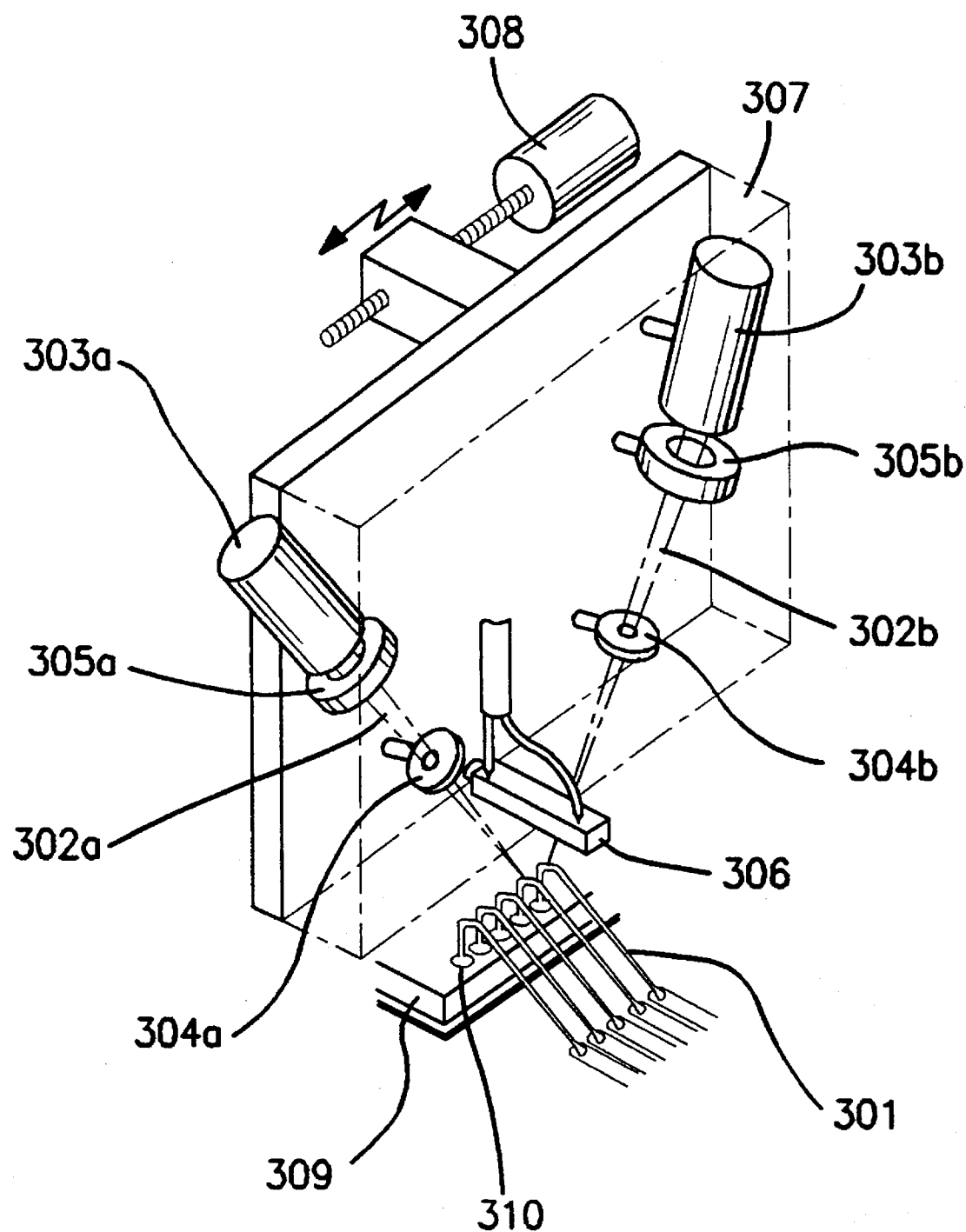
FIG. 3 is a perspective view showing a structure of a bonding-wire appearance inspecting apparatus according to a first embodiment of the present invention.
Figure 4:
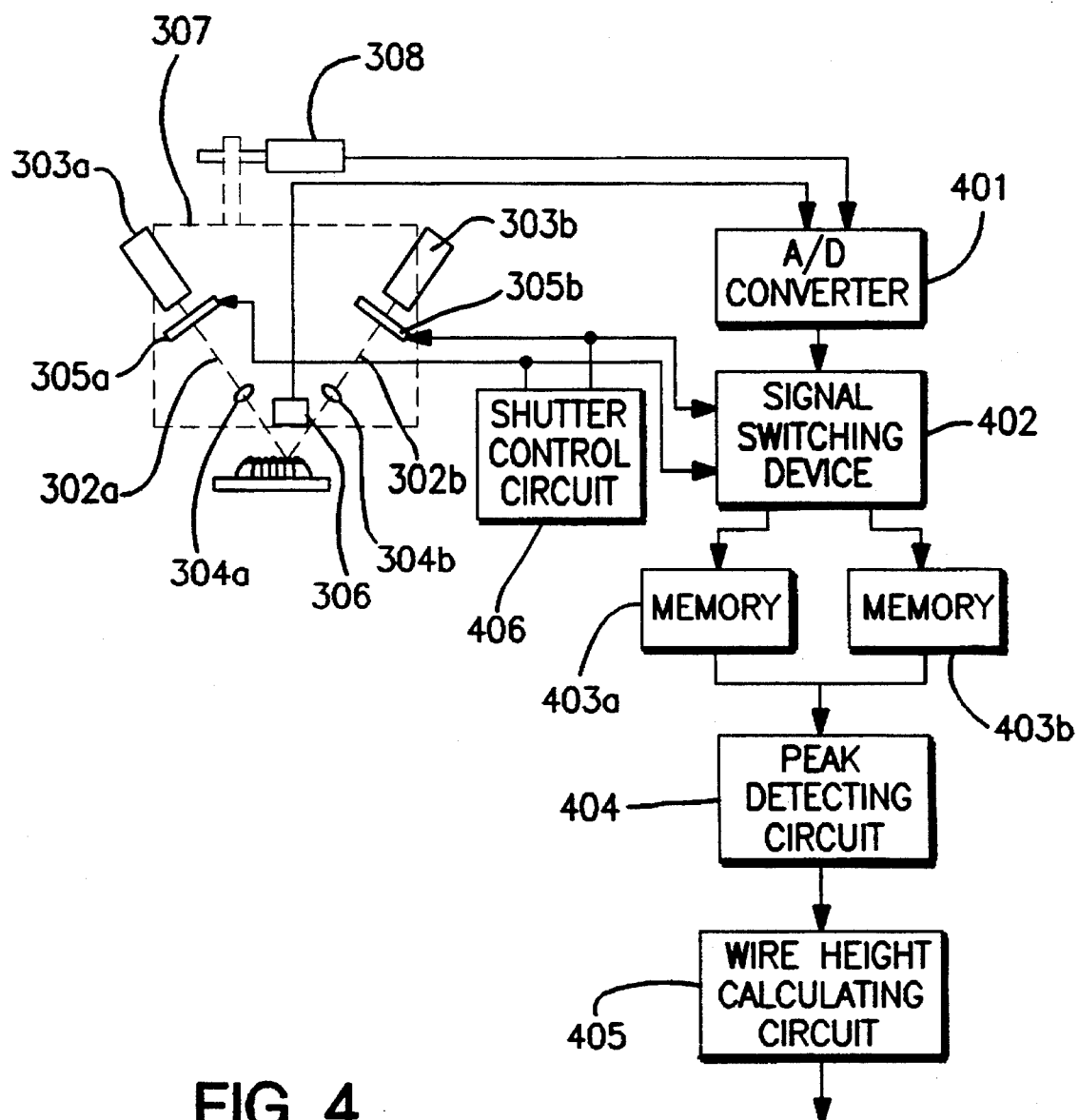
FIG. 4 is a schematic block diagram showing a signal process executed in the first embodiment of the present invention.

In FIG. 3, there is shown a structure of the appearance inspecting apparatus for the bonding-wire in accordance with the first embodiment. The bonding-wire appearance inspecting apparatus is comprised of a laser light source 303a for emitting a laser beam 302a to illuminate a bonding-wire 301 to be inspected, and another laser light source 303b for emitting a laser beam 302b to illuminate the bonding-wire 301. The laser beam 302b has an optical axis different from that of the first-mentioned laser beam 302a. This first inspecting apparatus is further constructed of a condenser lens 304a for condensing the laser beam 302a to be focused onto a predetermined focusing point, another condenser lens 304b for condensing the laser beam 302b to be focused onto a predetermined focusing point, a shutter 305a arranged in the optical path of the laser beam 302a, and another shutter 305b arranged in the optical path of the laser beam 302b. The first inspecting apparatus further includes a photodetector 306 arranged above and near the bonding-wire 301, which detects laser light reflected from the bonding-wire 301 and originated from the laser beams 302a and 302b, and a scanning mechanism for scanning such an optical head 307 along a horizontal direction with respect to the bonding-wire 301, on which there are mounted the laser light sources 303*a* and 303*b*, the condenser lens 304*a* and 304*b*, the shutter 305*a* and 305*b*, and the photodetector 306. It should be noted that a predetermined reference position where either the laser beam 302*a* or the laser beam 302*b* is focused by way of the condenser lens 304*a* or 304*b*, may be set as such a height that, for instance, the bonding-wire 301 having the normal shape should be located. Also, it is possible to set as the reference position, a height of an upper surface of a semiconductor chip 309 on which the bonding-wire 301 has been bonded.

Both of the laser beams 302*a* and 302*b* are emitted from the upper position of the bonding-wire 301 at a certain inclined angle. The laser light sources 303*a* and 303*b* are positioned in such a manner that planes formed by the laser beams 302*a* and 302*b* are located parallel to a pad array 310 of the semiconductor chip 309. Further, these laser light sources 303*a* and 303*b* are so arranged that the optical paths of the laser beams 302*a* and 302*b* are located in a symmetrical manner with respect to a vertical axis for a stage on which the semiconductor chip 309.

The photodetector 306 preferably has a line-shaped light receiving surface, and also a sufficiently elongated shape. The photodetector 306 is positioned above and near the bonding-wire 301 within such a range where the laser beams 302*a* and 302*b* are not intercepted by the photodetector 306. The photodetector 306 is arranged in such a manner that the longitudinal direction of the light receiving surface thereof is located perpendicular to the planes formed by the laser beams 302*a* and 302*b*. With such an arrangement of the photodetector 306, the laser light of the laser beams 302*a* and 302*b* regular-reflected from the semiconductor chip 309 and the like is hardly incident upon the photodetector 306, but only the reflection light of these laser beams 302*a* and 302*b* regular-reflected from the bonding-wire 301 is detected by the photodetector 306. In other words, an amount of the reflection light detected by the photodetector 306 indicates a peak value when either the laser beam 302*a* or the laser beam 302*b* is regular-reflected from the bonding-wire 301. This is because a sectional shape of the bonding-wire 301 is circular. There are various sorts of loop shapes of the bonding-wire 301, so that the directions of the laser reflection light the bonding-wire 301 are greatly changed in accordance with the shape of this loop. However, as previously described in the first embodiment of the present invention, since the photodetector 306 having the line-shaped light receiving plane which is formed as an elongate shape along the direction perpendicular to the planes formed by the laser beams 302*a* and 302*b* is arranged above and near the bonding-wire 301, the reflection light along the various directions perpendicular to the direction of the pad array 310 can be detected by the photodetector 306.

Referring now to FIG. 3 to FIG. 6, operations of the bonding-wire appearance inspecting apparatus according to the first embodiment will be described.

Figure 6:
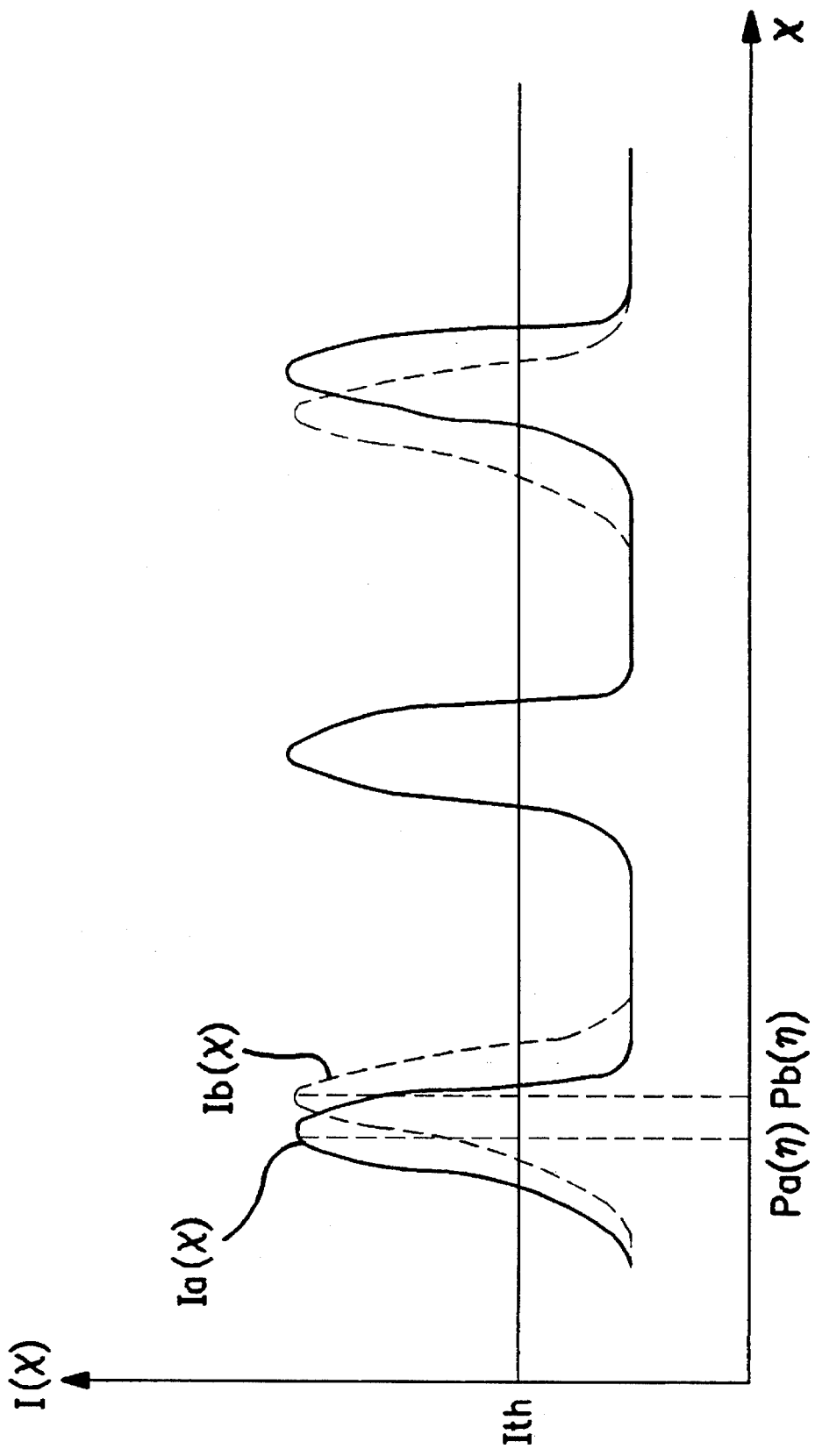
FIG. 6 is a waveform chart showing a reflection light signal according to the first embodiment of the present invention.
Figure 7:
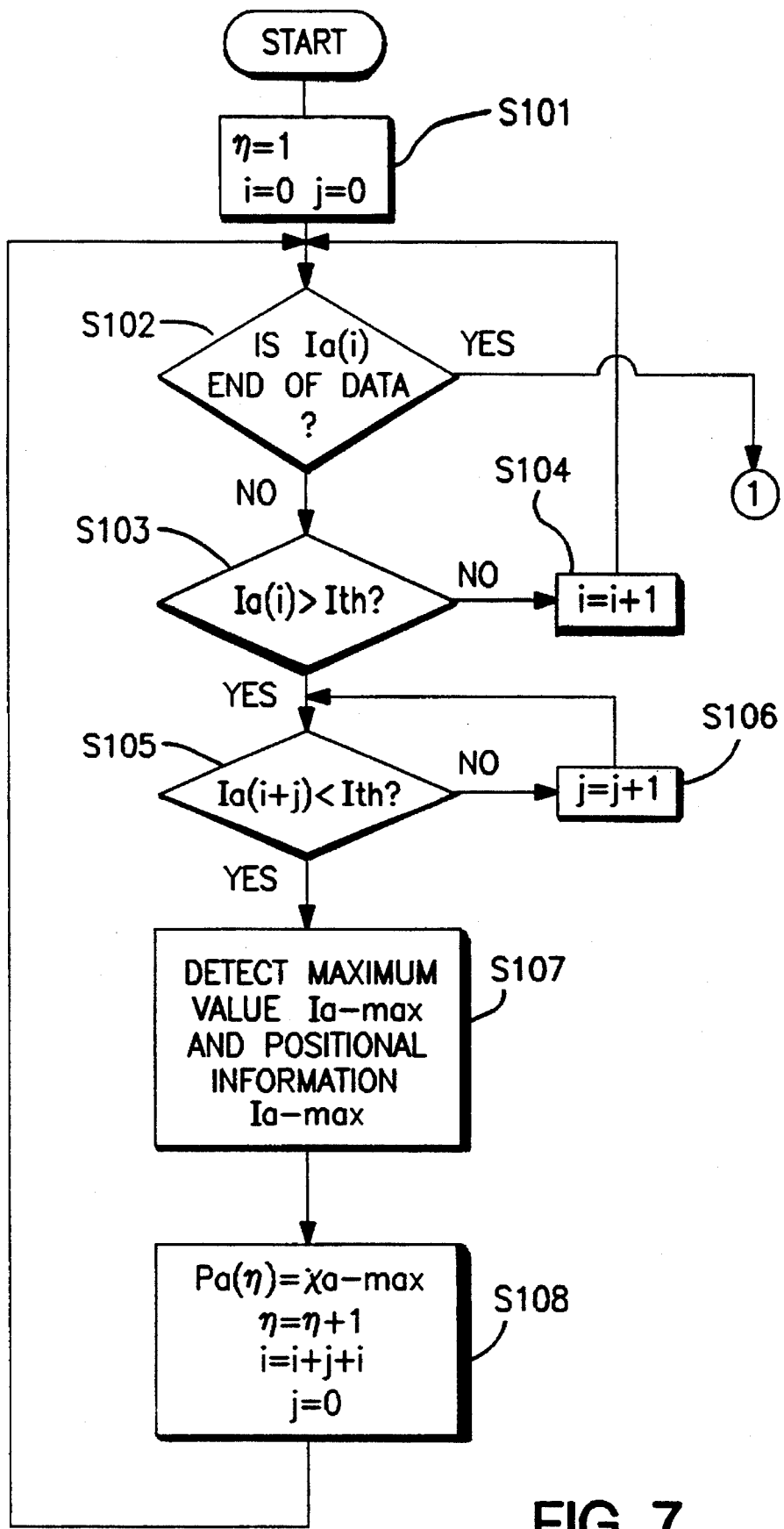
FIG. 7 to FIG. 9 are flow charts showing operation sequences effected in the first embodiment of the present embodiment.
Figure 8:
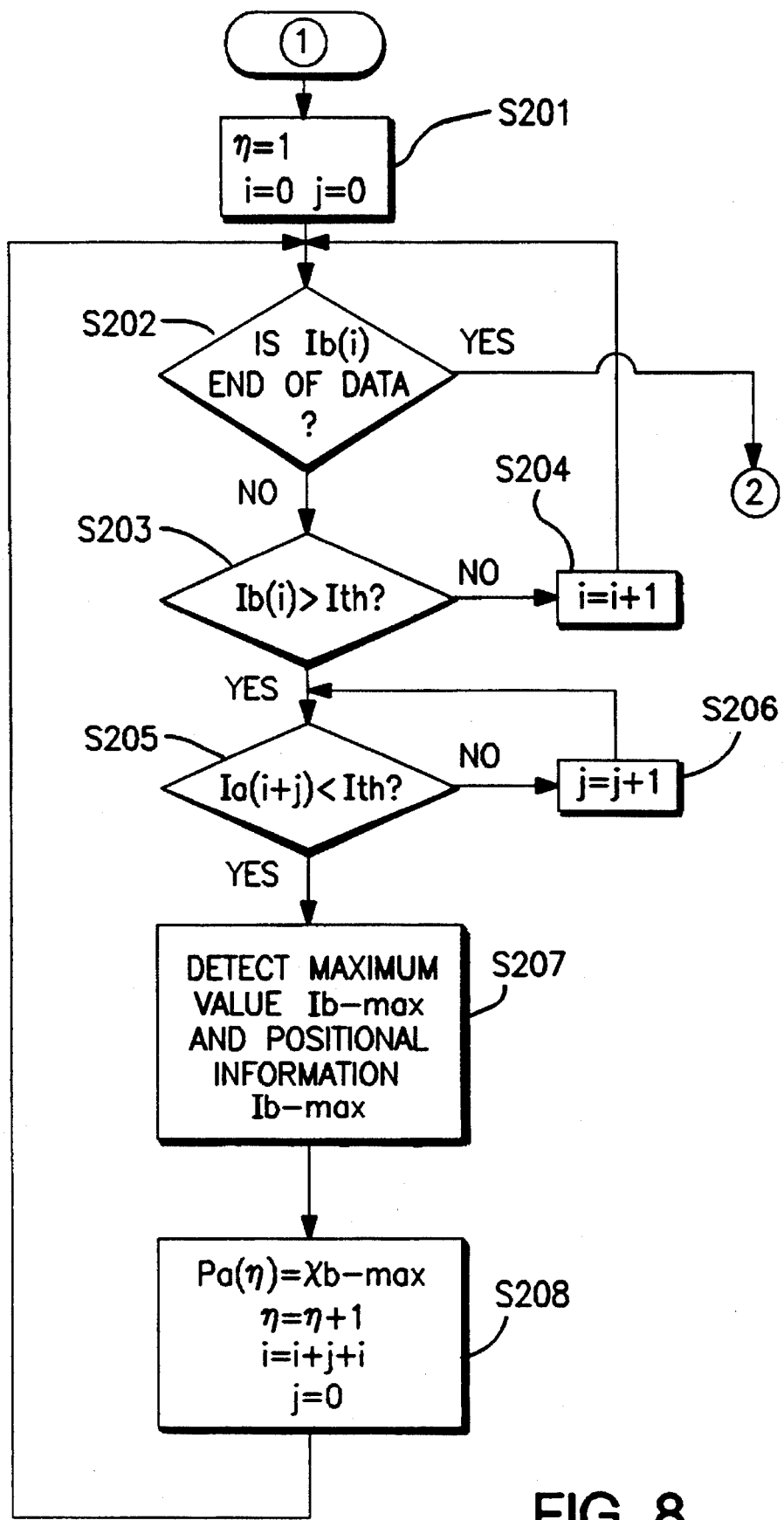
Figure 9:
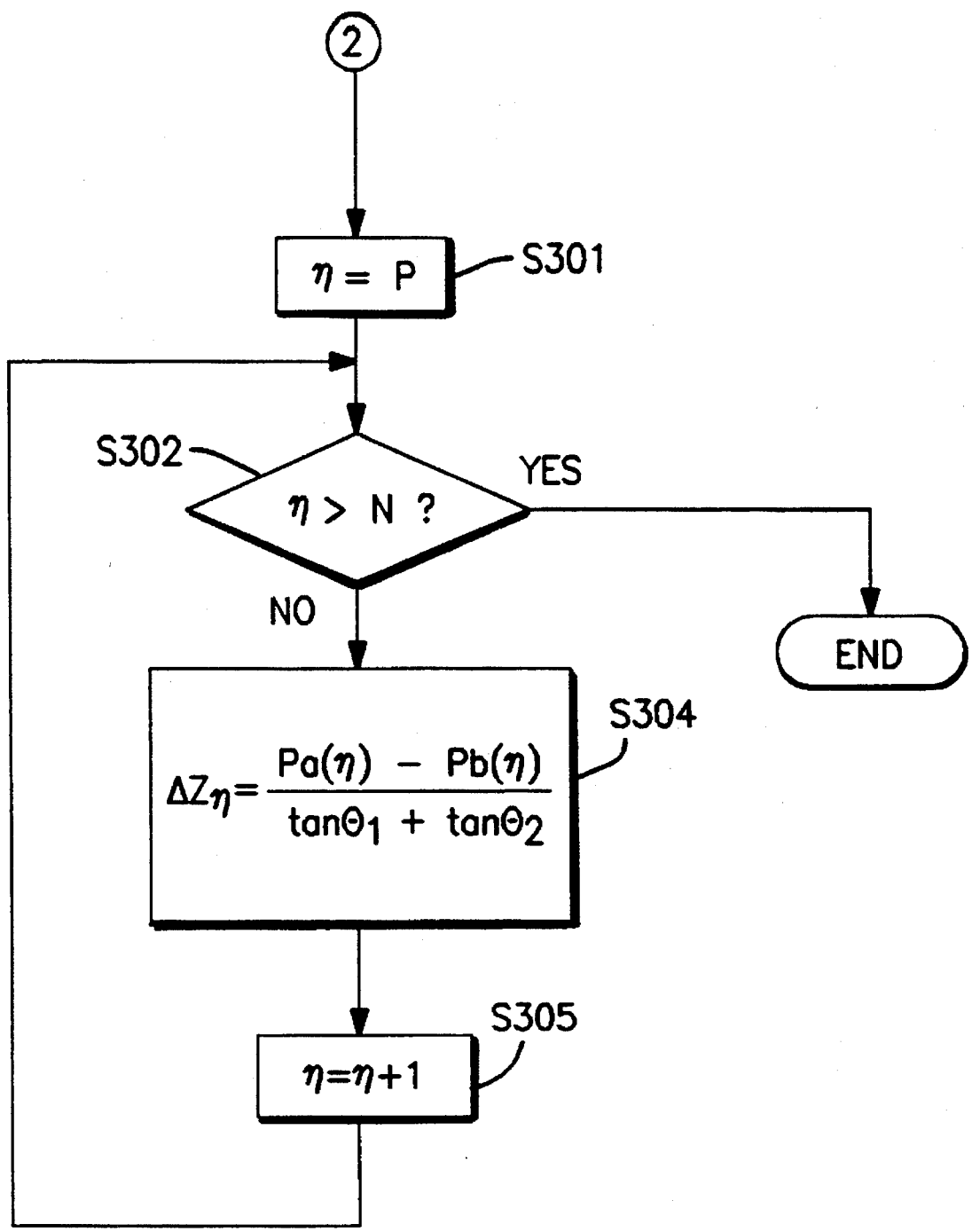

While the optical head 307 is relatively transported by the scanning mechanism 308 with respect to the bonding-wire 301, the laser light originated from the laser beam 302*a* or 302*b* and reflected from the bonding-wire 301 is detected by the photodetector 306. A reflection light signal output from the photodetector 306 is converted by an A/D convertor 401 into a corresponding digital signal in synchronism with a pulse series (see FIG. 5D) produced from an encoder of the scanning mechanism 308. The digital reflection signal derived from the A/D convertor 401 is switched by a signal switching device 402 in such a manner that the digital reflection signal obtained from the reflection light of the laser beam 302*a* is stored into a memory 403*a*, whereas the digital reflection signal obtained from the reflection light of the laser beam 302*b* is stored into a memory 403*b*. As illustrated in FIG. 6, the reflection light signals corresponding to the relative position of the optical head 307 with respect to the bonding-wire wire 301 are stored into the respective memories 403*a* and 403*b*. As apparent from the signal waveform shown in FIG. 6, plural peaks of the reflection light signals are present, which are caused by detecting the reflection light corresponding to a plurality of bonding-wires 301 by the photodetector 306, since the optical head 307 is transported by the scanning mechanism 308. A peak detecting circuit 404 detects a peak of a reflection light amount corresponding to the reflection light reflected from the bonding-wire 301 based on the digital reflection light signal stored in the memory 403*a*. Then, the peak detecting circuit 404 detects a first relative position (will be referred to a "peak position" hereinafter) of the optical head 307 with respect to the bonding-wire 301 when the reflection light amount indicates the peak. Similarly, the peak detecting circuit 404 detects a peak of a reflection light amount corresponding to the reflection light on the bonding-wire 301 based on the reflection light signal stored in the memory 403*b*. Then, the peak detecting circuit 404 detects a second relative position of the optical head 307 with respect to the bonding-wire 301 when the reflection light amount indicates the peak. A wire height calculating circuit 405 calculates a height of the bonding-wire 301 based upon a difference between the first peak position of the reflection light signal of the laser beam 302*a* and the second peak position of the reflection light signal of the laser beam 302*b*.

In the above-described first embodiment of the present invention, in order that the reflection light of the laser beam 302*a* and the reflection light of the laser beam 302*b* are independently detected by the photodetector 306 and then these detected reflection signals are stored into the respective memories 403*a* and 403*b*, the laser beams 302*a* and 302*b* are alternately emitted to the bonding-wire 301 by employing the shutter 305*a* and 305*b*. In other words, when an open signal (see FIG. 5B) is output from a shutter control circuit 406 to the shutter 305*a* and a close signal (see FIG. 5C) is output therefrom to the shutter 305*b*, the shutter 305*a* is opened to pass the laser beam 302*a* therethrough whereas the shutter 305*b* is closed to cut off the laser beam 302*b*. As a result, only the laser beam 302*a* is emitted to the bonding-wire 301. Under this condition, the optical head 307 is scanned by the scanning mechanism 308 along a predetermined direction at a preselected speed (see FIG. 5A), so that the reflection light of the laser beam 302*a* is detected by the photodetector 306. In response to the open signal output from the shutter control circuit 406 to the shutter 305*a*, the signal switching device 402 brings the memory 403*a* into a write enable condition (see FIG. 5E). On the other hand, in response to the close signal supplied from the shutter control circuit 406 to the shutter 305*b*, the signal switching device 402 brings the memory 403*b* into a write unable condition (see FIG. 5F). As a consequence, the reflection light signal of the laser beam 302*a* which has been detected by the photodetector 306 and then A/D-converted into the digital signal by the A/D convertor 401 can be stored into the memory 403*a*. When this process is accomplished, the shutter control circuit 406 conversely outputs the close signal (see FIG. 5B) to the shutter 305*a* and the open signal (see FIG. 5C) to the shutter 305*b*. Accordingly, the shutter 305*a* is closed to cut off the laser beam 302*a* whereas the shutter 305b is opened to pass the laser beam 302b therethrough. As a consequence, only the laser beam 302b is emitted to the bonding-wire 301. Under this condition, the optical head 307 is again scanned by the scanning mechanism 308 along a direction opposite to the above-described direction during the first scanning operation at a preselected speed (see FIG. 5A), and then the reflection light of the laser beam 302b is detected by the photodetector 306. As described above, since the scanning direction of the optical head 307 when the reflection light of the laser beam 302b is detected is selected to be opposite to the scanning direction of the optical head 307 when the reflection light of the laser beam 302a is detected, the processing time can be shortened. Alternatively, it should be understood that the optical head 307 may be scanned twice along the same direction. The signal switching device 402 brings the memory 403b into the write enable state (see FIG. 5F) in response to the open signal output from the shutter control circuit 406 to the shutter 305b, and on the other hand, brings the memory to 403a into the write unable state (see FIG. 5E) in response to the close signal supplied to the shutter 305a. Accordingly, the reflection signal of the laser beam 302b which has been detected by the photodetector 306 and A/D-converted into the digital signal can be stored into the memory 403b.

Referring now to FIG. 4 and FIG. 6 to FIG. 10, operations of the peak detecting circuit 404 and the wire height calculating circuit 405 will be explained, and further a principle to calculate the height of the bonding-wire measured from a reference position will be explained. It should be understood that a "reference position" is such a position where the laser beams 302a and 302b are mutually condensed and intersected with each other. For instance, the reference position is set either to such a height where the bonding-wire 301 having the normal shape should be located, or such a height of an upper surface of the semiconductor chip 309 on which the bonding-wire 301 is bonded.

As seen from FIG. 6, the reflection light signal Ia(x) of the laser beam 302a is stored in the memory 403a in accordance with the relative position of the optical head 307 with respect to the bonding-wire 301 (will be referred to "positional information" hereinafter). The peak detecting circuit 404 detects both of a peak of the reflection light signal Ia(x) and the positional information "x" when this peak is detected. In a flow chart of FIG. 7, after various parameters such as a sequence of the bonding-wires 301 to be inspected and the positional information "i", "j" of the optical head 307 are set as an initial condition (step S101), the peak detecting circuit 404 detects the positional information x (i≤x≤j) where the reflection light signal Ia(x) exceeds a threshold value Ith (steps S102 to S105). Then, the peak detecting circuit 404 detects a maximum value Ia-max of the reflection light signal Ia(x) within a range of i≤x≤j. Further, the peak detecting circuit 404 detects positional information Xa-max wherein the reflection light signal Ia(x) indicates the maximum value Ia-max (step S107). Then, the acquired positional information Xa-max is detected as positional information Pa(n) corresponding to the n-th bonding-wire (step S108). The above-described process operation is performed with respect to all of the reflection light signals Ia(x), so that either one or plural positional information Pa(n) (1≤n≤N) is detected. In this case, symbol "N" indicates the quantity of bonding-wire 301 to be inspected.

When the above-described process operation is completed with respect to the reflection light signal Ia(x) stored in the memory 403a, the peak detecting circuit 404 performs a process operation similar to the above-described process operation as to the reflection light signal Ib(x) (see FIG. 6) stored in the memory 404b. That is, referring to another flow chart of FIG. 8, the peak detecting circuit 404 detects both of a maximum value Ib-max within a predetermined range (i≤x≤j) of the reflection light signal Ib(x) of the laser beam 302b stored in the memory 403b, and positional information Xb-max of the optical head 307 when the maximum value Ib-max is obtained (steps S201 to S207). Then, the acquired positional information Xb-max is detected as positional information Pb(n) corresponding to the n-th bonding-wire 301 (step S208). The above-described process operation is executed with respect to all of the reflection light signals Ib(x), so that either one, or plural positional information Pb(n) (1≤n≤N) is detected.

When the above-explained process operation with respect to the reflection light signal Ib(x) stored in the memory 403b is completed, the wire height calculating circuit 405 calculates a height ΔZn of the bonding-wire 301 with regard to the reference position in accordance with the below-mentioned equation with employment of the positional information Pa(n) and Pb(n) detected by the peak detecting circuit 404. This height calculation process (step S304) will now be explained with reference to a flow chart of FIG. 9. The above-explained process operation is carried out for all of the bonding-wires 301 to be inspected.

$$\Delta Zn = \frac{Pa(n) - Pb(n)}{\tan\theta_1 + \tan\theta_2}$$

Figure 10:
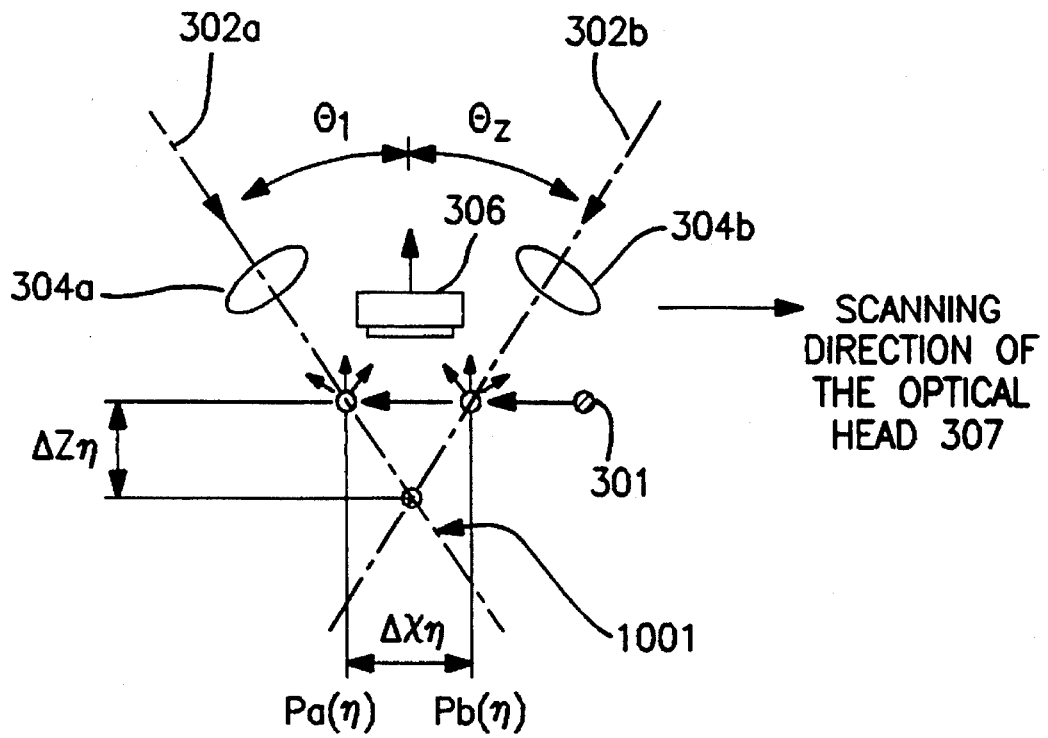
FIG. 10 is a schematic diagram showing an explanation of a basic operation according to the first embodiment of the present invention.

In this equation, symbol "ΔZn" indicates a height of the n-th bonding-wire 301 measured from the reference position, and symbols "θ1" and "θ2" represent inclinations of the laser beams 302a and 302b with respect to the Z-axis (see FIG. 10). Referring now to FIG. 10, while the optical head 307 is transported along the X-axis direction, when the relative position between the optical head 307 and the n-th bonding-wire 301 becomes Pa(n), the reflection light signal of the laser beam 302a indicates a peak. Also when the relative position between the optical head 307 and the n-th bonding-wire 301 becomes Pb(n), the reflection light signal of the laser beam 302b represents a peak. As a result, if a difference ΔXn (Pa(n)–Pb(n)) between two sets of positional information Pa(n) and Pb(n), and also the trigonometric function are utilized, then it is possible to conduct such an equation to calculate the height ΔZn of the bonding-wire 301 measured from a reference position 1001 where the laser beam 302a is intersected with the laser beam 302b. In accordance with the first embodiment of the present invention, since the height of the bonding-wire with respect to the reference position can be detected in accordance with such a simple calculation formula, the structure of the first bonding-wire appearance inspecting apparatus can be made simple and further the high processing speed thereof can be realized.

Figure 11:
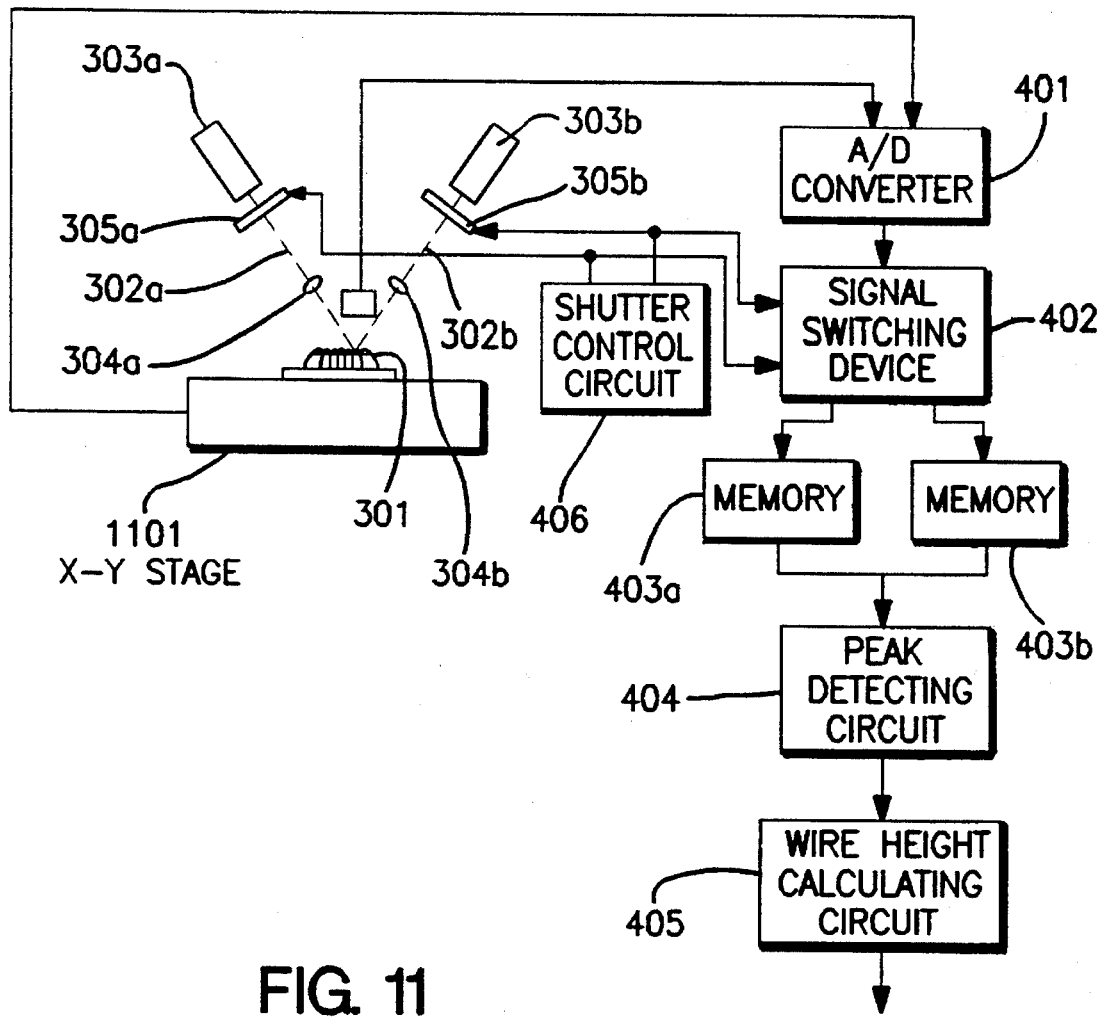
FIG. 11 is a schematic diagram showing a structure of a bonding-wire appearance inspecting apparatus according to a second embodiment of the present invention.

Referring now to FIG. 11, a bonding-wire appearance inspecting apparatus according to a second embodiment of the present invention will be described.

In the first embodiment, as previously described, the scanning mechanism 308 transporting the optical head 307 is employed. In contrast, according to the second embodiment of the present invention, the semiconductor chip 309 to which the bonding-wire 301 has been bonded is mounted on an X-Y stage 1101, and the X-Y stage 1101 is transported, whereby a relative position between the optical unit constructed of the laser source 303a, 303b and the photodetector 306, and the bonding-wire 301 is moved. Then, the reflection light signals from the laser beams 302a and 302b, which are detected from the photodetector 306, are converted into the digital reflection light signals by the A/D convertor 401 in synchronism with a pulse series output from an encoder employed in the X-Y stage 1101. Since the subsequent process operations are similar to those of the first embodiment, no further explanations thereof are made.

Figure 12:
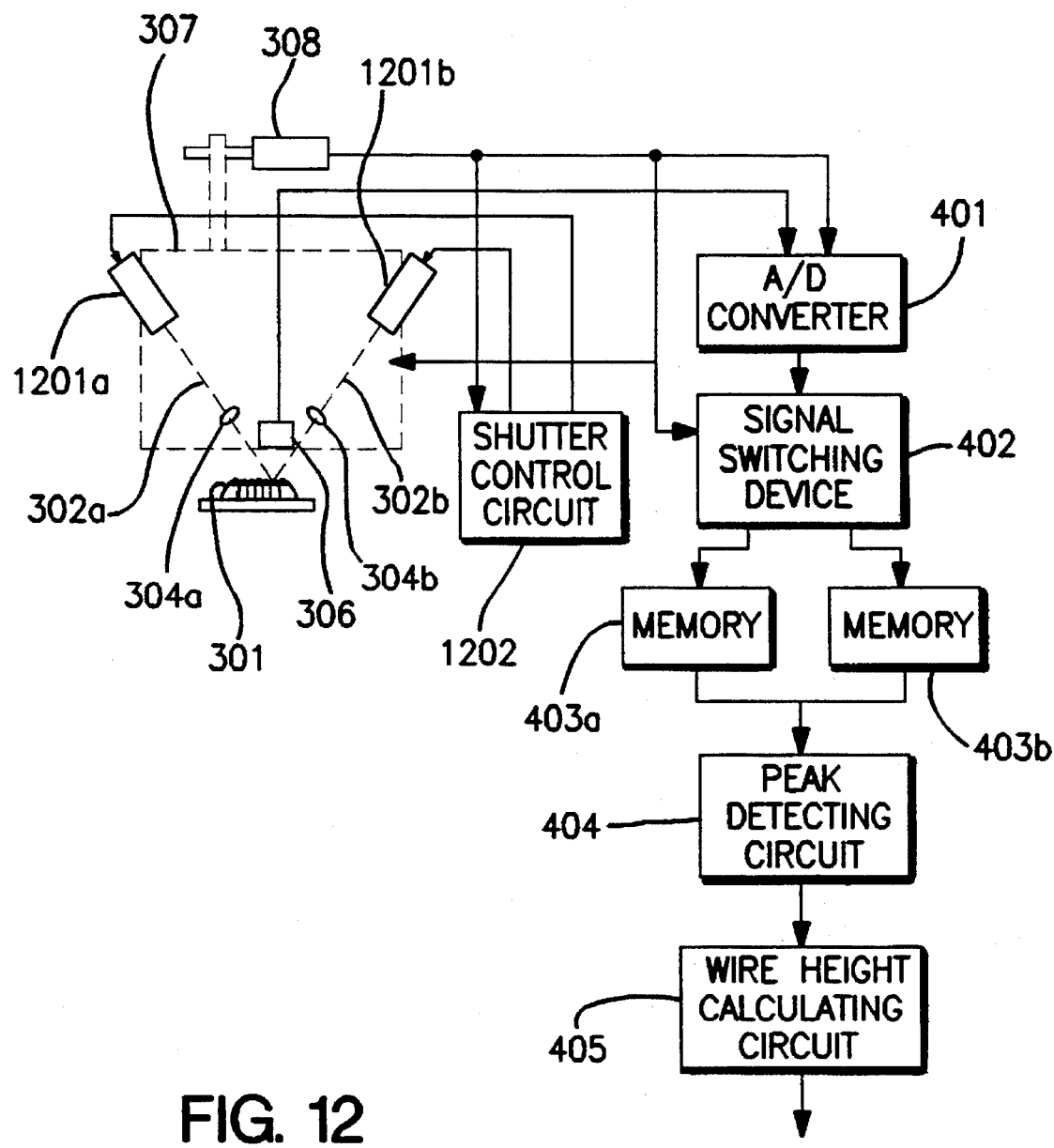
FIG. 12 is a schematic diagram showing a signal process performed in accordance with a third embodiment of the present invention.

With reference to FIG. 12 and FIG. 13, a bonding-wire appearance inspecting apparatus according to a third embodiment of the present invention will be described.

In accordance with the third embodiment, semiconductor lasers which can be modulated at high speeds are applied to two sets of the above-explained laser sources employed in the first embodiment. Semiconductor lasers 1201a and 1201b are controlled in a highspeed switching mode by a laser driving circuit 1202, and thus laser beams 302a and 302b derived from these semiconductor lasers 1201a and 1201b are emitted to the bonding-wire 301 in the time divisional manner during one scanning operation of the optical head 307 by the scanning mechanism 308. The photodetector 306 separately detects reflection light of the laser beam 302a and reflection light of the laser beam 302b. A reflection light signal output from the photodetector 306 is converted by the A/D convertor 401 into a digital signal in synchronism with the pulse series produced from the encoder of the scanning mechanism 308. In synchronism with the timings at which the laser beams 302a and 302b are emitted in the time divisional manner, the signal switching device 402 switches the digital signal derived from the A/D convertor 401 in such a manner that the reflection light signal of the laser beam 302a is stored in the memory 403a, and also the reflection light signal of the laser beam 302b is stored in the memory 403b. Since the subsequent process operations are similar to those of the first embodiment, no further explanations thereof are made. With the above-described arrangement, the height of the bonding-wire 301 from the reference position can be detected by scanning the optical head 307 only 1 time by the scanning mechanism 308. As a consequence, the time duration required to inspect the appearance of the bonding-wire 301 can be considerably reduced.

Figures 13D, 13E, 13F:
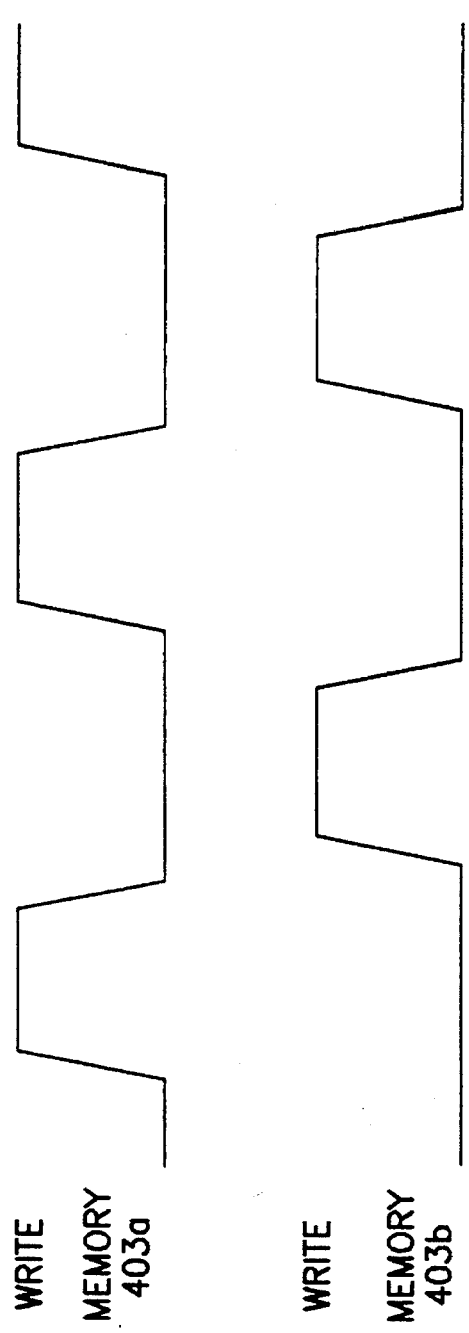
FIG. 13D and 13E are timing charts showing writing enable timings of a memories.
FIG. 13F is a timing chart showing a data writing timing to memories.

With reference to FIG. 12 and FIG. 13, when such a scanning mechanism 308 having positional resolution of 1 micrometer and a scanning speed of 100 mm/sec., is employed, a pulse having a frequency of 100 KHz produced from the encoder of the scanning mechanism 308 is output to an A/D convertor 401, a signal switching device 402, and the laser driving circuit 1202 every time the optical head 307 is transported by 1 micrometer (see FIG. 13A). The laser driving circuit 1202 drives the two semiconductor lasers 1201a and 1201b by shifting the phases thereof by 180° in response to a rectangular wave having a frequency of 50 KHz in synchronism with the pulse series (see FIG. 13B and FIG. 13C). The A/D convertor 401 samples the reflection light signals of the laser beams 302a and 302b detected by the photodetector 306 in a time period of 100 KHz in synchronism with the pulse series. The signal switching device 402 causes the memory 403a to be under write enable state and conversely the memory 403b to be under write unable state when the semiconductor laser 1201a is driven in synchronism with the pulse series. Similarly, the signal switching device causes the memory 403a to be under write unable condition and the memory 403b to be under write enable condition when the semiconductor laser 1201b is driven in synchronism with the pulse series (see FIG. 13D and FIG. 13E). As a result, the reflection light signals of the laser beams 302a and 302b detected by the photodetector 306 are alternately stored in the memory 403a and the memory 403b in synchronism with the pulse series (see FIG. 13F).

It should be understood that since the semiconductor lasers 1201a and 1201b are applied as the laser light source, the laser beams 302a and 302b are illuminated to the bonding-wire 301 in the time divisional manner in the third embodiment of the present invention. Alternatively, a similar operation may be achieved by employing such a highspeed modulatable element as an acoustic-optical modulator as the shutters 305a and 305b as in the first embodiment.

Figure 14:
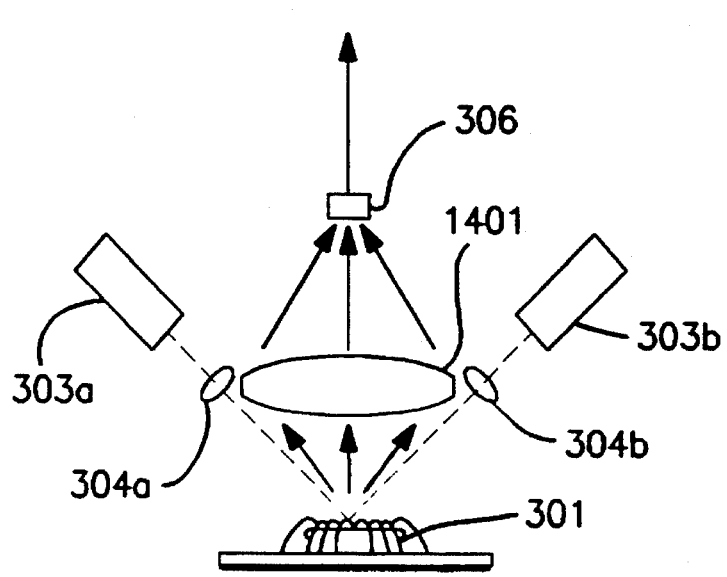
FIG. 14 is a schematic diagram showing a structure of a major portion according to a fourth embodiment of the present invention.

Next, a bonding-wire appearance inspecting apparatus according to a forth embodiment of the present invention will now be explained with reference to FIG. 14.

A feature of a fourth embodiment of the present is to arrange a light receiving lens 1401 having a wide light receiving angle between the bonding-wire 301 to be inspected and the photodetector 306 detecting the reflection right of the respective laser beams 302a and 302b reflected from the bonding-wire 301. Since the reflection light of the laser beams 302a and 302b reflected from the bonding-wire 301 along various directions is condensed by using the light receiving lens 1401 to the photodetector 306 arranged at the focusing position of the light receiving lens 1401, the light receiving area of the photodetector 306 can be reduced. Furthermore, such bonding-wires 301 having various loop shapes can be inspected in higher precision. It is preferable to employ an spherical lens as the light receiving lens 1401 so as to widen the light receiving angle. It should be noted that arrangement of the fourth embodiment other than the above-described arrangement may be applied to similar arrangements of the first, second, or third embodiment.

Figure 15:
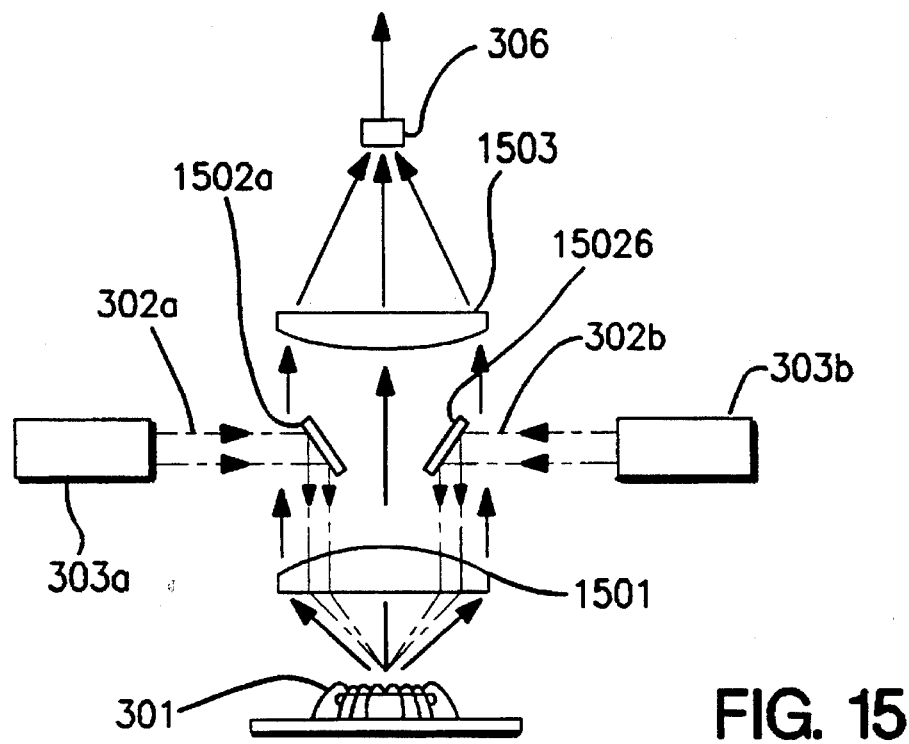
FIG. 15 is a schematic diagram showing a structure of a major portion according to a fifth embodiment of the present invention.
Figure 16:
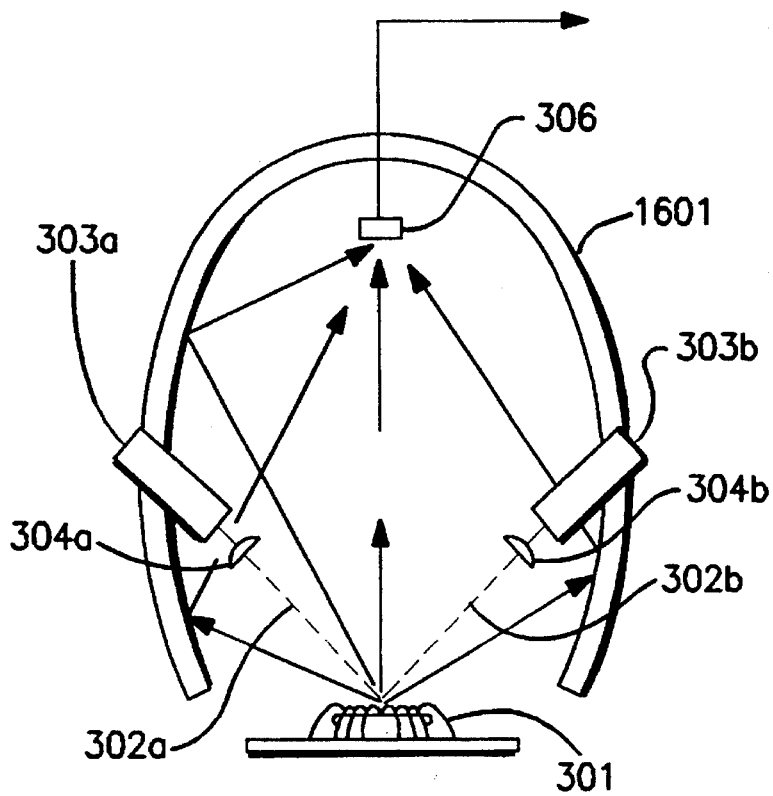
FIG. 16 is a schematic diagram showing a structure of a major portion according to a sixth embodiment of the present invention.

Next, a bonding-wire appearance inspecting apparatus according to a fifth embodiment of the present invention will now be explained with reference to FIG. 15.

That is, the bonding-wire inspecting apparatus of the fifth embodiment of the invention comprises a light receiving lens 1501 positioned in such a way that the location of the bonding-wire 301 corresponds to a focal position thereof, a reflection mirror 1502a for conducting the laser beam 302a emitted from the laser light source 303a to the light receiving lens 1501, and another reflection mirror 1502b for conducting the laser beam 302b emitted from the laser light source 303b into the light receiving lens 1501. The inspecting apparatus further contains a focusing lens 1503 for focusing the reflection light originated from the laser beams 302a and 302b reflected from the bonding-wire 301, which have been formed as parallel light by the light receiving lens 1501, and also a photodetector 306 located at the focusing position of the focusing lens 1503. With such a structure, it is no longer required to arrange a condenser lens for condensing either the laser beam 302a or the laser beam 302b to the bonding-wire 301. As a consequence, since the light receiving lens 1501 can be positioned near the bonding-wire 301 without any optical interface with the condenser lens, the light receiving angle of the light receiving lens 1501 can be easily widened.

Similarly, as the other arrangements of the fifth embodiment, the previously explained constructive arrangements in the first, second, or third embodiment may be applied.

Next, a description will be made of a bonding-wire appearance inspecting apparatus according to a sixth embodiment of the present invention.

The bonding-wire appearance inspecting apparatus of the sixth embodiment comprises an elliptical reflection mirror 1601 arranged in such a manner that the position of the bonding-wire 301 which is coincident with the focal point of the laser beam 302a and the focal point of the laser beam 302b becomes a first focal position thereof. Then, the photodetector 306 is arranged at a second focal position of the elliptical reflection mirror 1601, so that various reflection light of the laser beams 302*a* and 302*b* reflected from the bonding-wire 301 along various directions can be condensed to the photodetector 306. As a result, the light receiving area of the photodetector 306 can be made small. Furthermore, since the elliptical mirror 1601 owns no spherical aberration, the light receiving angle can be readily widened, as compared with that of such a case that the reflection light is condensed by using the light receiving lens system. Accordingly, the reflection light of the laser beams 302*a* and 302*b* reflected along the various directions can be detected at higher efficiency. It should also be noted that as the other constructive arrangements of the sixth embodiment, the previously explained similar arrangements employed in the first, second, or third embodiment may be applied.

Figure 17:
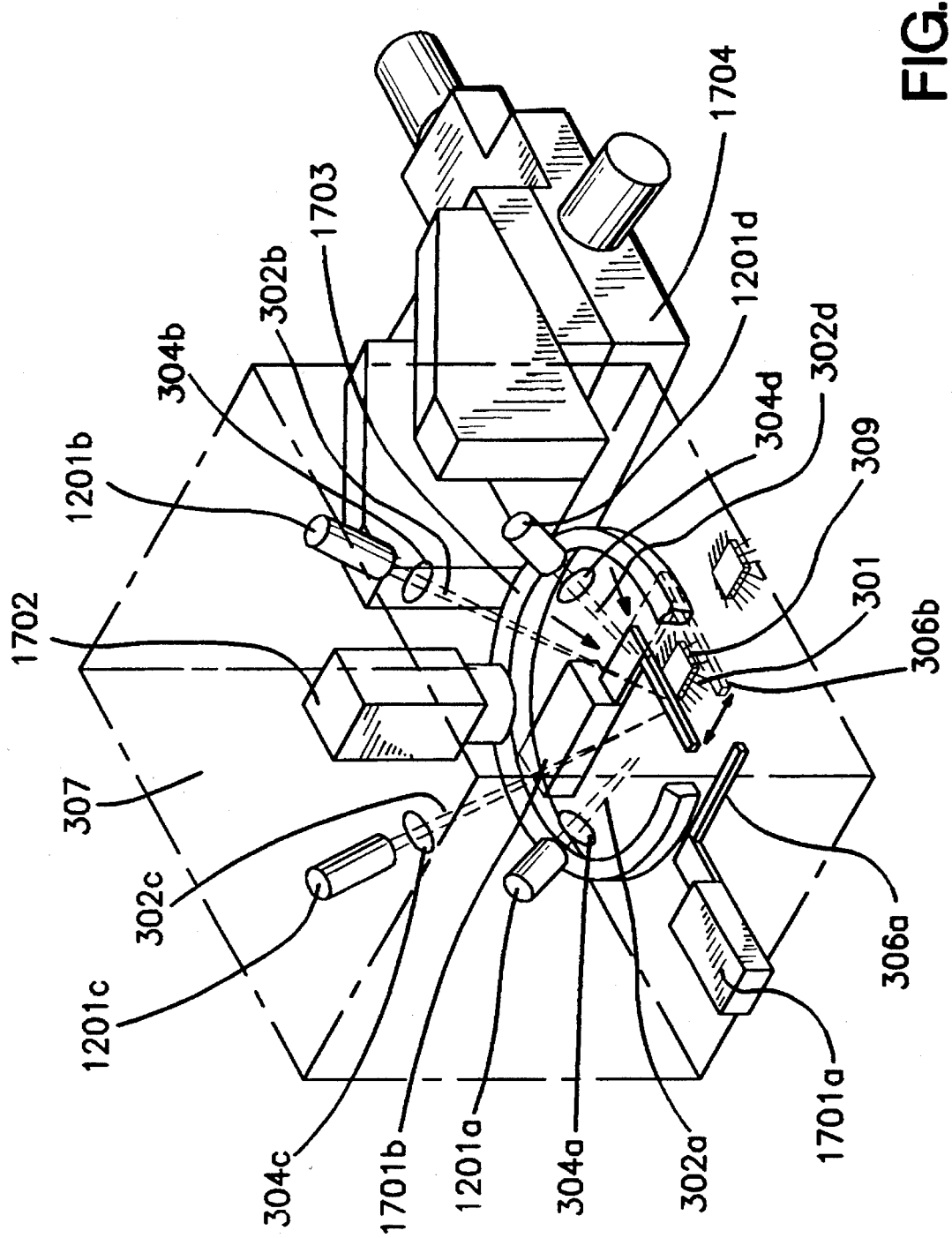
FIG. 17 is schematic diagram showing a structure of a major portion according to a seventh embodiment of the present invention.

Subsequently, with reference to FIG. 17, another bonding-wire appearance inspecting apparatus of a seventh embodiment of the present invention will now be explained.

According to the seventh embodiment, heights of the bonding-wires 301 bonded on four edges of the semiconductor chip 309 measured from the reference position can be easily detected without changing the setting direction of this semiconductor chip 309. That is to say, semiconductor lasers 1201*a*, 1201*b* and condenser lenses 304*a*, 304*b* are so arranged that a plane formed by the laser beams 302*a* and 302*b* emitted from these semiconductor laser 1201*a*, 1201*b* is positioned in parallel to pad arrays which are provided along two opposite edges of the semiconductor chip 309. On the other hand, semiconductor lasers 1201*c*, 1201*d* and condenser lenses 304*c*, 304*d* are so arranged that a plane formed by the laser beams 302*c* and 302*d* emitted from these semiconductor laser 1201*c*, 1201*d* is positioned in parallel to pad arrays which are provided along two opposite edges of the semiconductor chip 309, which are different from the first-mentioned two edges. Reflection light of the laser beams 302*a* and 302*b* from the bonding-wire 301 is detected by the photodetector 306*a*. On the other hand, reflection light of the laser beams 302*c* and 302*d* is detected by the photodetector 306*b*. It should be noted that the photodetectors 306*a* and 306*b* have line-shaped light receiving surfaces, respectively. The photodetector 306*a* is arranged perpendicular to a plane formed by the laser beams 302*a* and 302*b*, whereas the photodetector 306*b* is arranged perpendicular to a plane formed by the laser beams 302*c* and 302*d*. Furthermore, the photodetector 306*a* is mounted on a slider 1701*a*, and the other photodetector 306*b* is mounted on another slider 1701*b*. The optical head 307 containing these semiconductor lasers 1201*a*, 1201*b*, 1201*c*, 1201*d* and the photodetectors 306*a*, 306*b* is relatively transported by a two-axial scanning mechanism 1704 along the perpendicular two edges of the semiconductor chip 309.

In the seventh embodiment with the above-described structure, an shape of the bonding-wire 301 is inspected by employing the optical system constructed of the semiconductor lasers 1201*a*, 1201*b* and the photodetector 306*a*, while the optical head 307 is transported by the two-axial scanning mechanism 1704 along the X-axis direction. Subsequently, another shape of the bonding-wire 301 is inspected by employing the optical system arranged by the semiconductor lasers 1201*c* and 1201*d*, and the photodetector 306*b*, while the optical head 307 is transported by the two-axial scanning mechanism 1704 along the Y-axis direction. Here, the sliders 1701*a* and 1701*b* are used in such a way that only the photodetector 306*a* or 306*b* used to inspect the shape of the bonding-wire 301 is moved to the inspecting position, and conversely, either the photodetector 306*a* or 306*b* not used in this inspection are moved from the bonding-wire 301 to the saving position in order not to establish optical interference with other optical devices.

Furthermore, according to the seventh embodiment of the present invention, since both of the photodetector 306*a* and the photodetector 306*b* can be saved from the position above the bonding-wire 301 to other positions, a two-dimensional imaging devices 1702 may be installed on the bonding-wire 301. That is, the imaging device 1702 is located above the bonding-wire 301, and an illumination device 1703 illuminating the bonding-wire 301 is arranged in, for example, a ring shape. The illumination device 1703 is so arranged that the illumination device 1703 does not intercept with other optical devices. With such an arrangement, it is also possible to inspect the positional shift of the bonding-wire 301 within the horizontal plane based upon the image data obtained from the imaging device 1702. When the shape of the bonding-wire 301 is inspected by using the two-dimensional imaging device 1702, both of these photodetectors 306*a* and 306*b* are saved out from the imaging area of the imaging device 1702 by way of the sliders 1701*a* and 1701*b*. As described above, not only the height of the bonding-wire 301 from the reference position is inspected, but also the positional shift of the bonding-wire 301 within the horizontal plane is inspected. Thus three-dimensional loop shape of the bonding-wire 301 can be inspected in high precision and in high speed.

Also, it should be understood that in the first to third embodiment, that when a means for saving the photodetector 306 from the position above the bonding-wire 301 to other positions is provided, both of such imaging device 1702 and illuminating device 1703 may be installed over the bonding-wire 301.

Figure 18C:
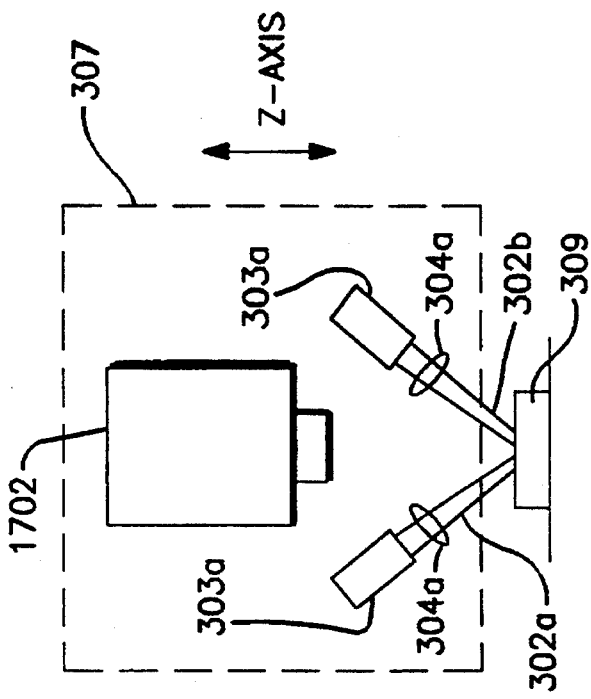
FIG. 18C is an explanatory diagram showing a state of laser beams when a reference height is adjusted.
Figure 18D:
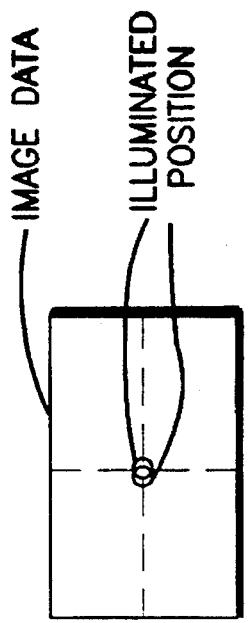
FIG. 18D is an image diagram obtained by two-dimensional imaging means when a reference height is adjusted.
Figure 18A:
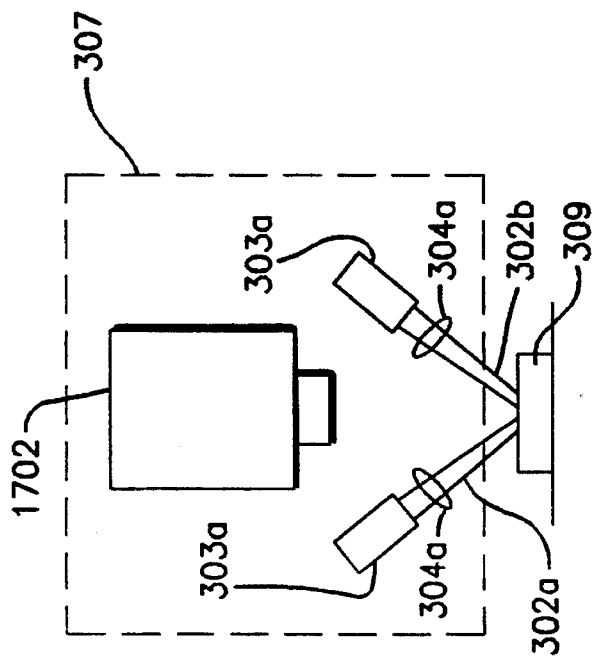
FIG. 18A is an explanatory diagram showing a state of laser beams before a reference height is adjusted.
Figure 18B:
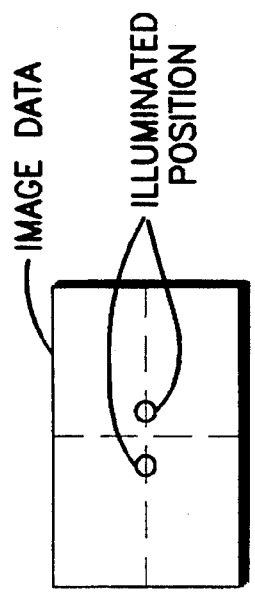
FIG. 18B is an image diagram obtained by two-dimensional imaging means before a reference height is adjusted.

As described above, when the imaging device 1702 is provided above the bonding-wire 301, it is very easily possible to change the reference position utilized when the height of the bonding-wire 301 is measured by utilizing the image data obtained from the imaging device 1702. When the height of the upper surface of the semiconductor chip 309 is set to be as the reference position, just after changing the type of the semiconductor chip 309, the position where the laser beams 302*a* and 302*b* are intersected with each other is not coincident with the position of the upper surface of the semiconductor chip 309, as illustrated in FIG. 18A. Under such a condition, the two-dimensional image data derived from the imaging device 1702 under such a condition is illustrated as in FIG. 18B, so that based on this image data, it is possible to detect such a fact that the laser beams 302*a* and 302*b* are emitted to separate positions over the semiconductor chip 309. Thus, as illustrated in FIG. 18D the optical head 307 is transported along the Z-axis direction to make the laser beams 302*a* and 302*b* coincide with each other on the semiconductor chip 309. The reference position may be readily set to the height of the upper surface of the semiconductor chip 309 newly positioned.

Although the bonding-wires 301 bonded on the semiconductor chip 309 has been employed for the shape inspection in the above-described embodiments, the present invention is not limited thereto, and can be employed for wire-shaped articles such as lead terminals, line materials, pipes and tubes.

What is claimed is:

1. A wire appearance inspecting apparatus comprising:

a first light source for emitting a first beam;

a second light source for emitting a second beam intersecting with said first beam at a preselected reference position;

light condensing means for condensing said first and second beams to said reference position;

a photodetector for detecting reflection light of said first and second beams;

a scanning mechanism for relatively transporting a unit on which said first and second light sources, said light condensing means and said photodetector are provided with respect to a wire to be inspected; and wire height calculating means for calculating a height of said wire from said reference position based on an interval between a relative position of said unit for said wire when said photodetector detects the reflection light of the first beam from said wire, and another relative position of said unit for said wire when said photodetector detects the reflection light of said second beam from said wire.

2. A wire appearance inspecting apparatus as claimed in claim 1 wherein said photodetector has an elongate line-shaped light receiving surface in a direction perpendicular to a plane formed by the first and second beams.

3. A wire appearance inspecting apparatus as claimed in claim 1 wherein said scanning mechanism is a means for moving the relative position between said unit and said wire in parallel to a plane formed by said first and second beams.

4. A wire appearance inspecting apparatus as claimed in claim 3 wherein said scanning mechanism is a means for moving said unit.

5. A wire appearance inspecting apparatus as claimed in claim 3 wherein said scanning mechanism is a mounting plate for mounting said wire and capable of moving said wire along at least one axial direction.

6. A wire appearance inspecting apparatus as claimed in claim 1 wherein said photodetector independently detects the reflection light of the first beam and the reflection light of the second beam.

7. A wire appearance inspecting apparatus as claimed in claim 1, further comprising a means for alternately emitting said first and second beams.

8. A wire appearance inspecting apparatus as claimed in claim 7 further comprising:

a first shutter for intercepting said first beam;

a second shutter for intercepting said second beam; and shutter control means for alternately causing said first shutter and second shutter to intercept the first and second beams.

9. A wire appearance inspecting apparatus as claimed in claim 7 further comprising:

beam switching means for alternately switching said first and second beams every time said unit and said wire are relatively transported by a distance defined by positional resolution of said scanning mechanism.

10. A wire appearance inspecting apparatus as claimed in claim 9 wherein said beam switching means is an acoustic-optical element for repeatedly emitting and intercepting the first and second beams.

11. A wire appearance inspecting apparatus as claimed in claim 10, further comprising:

A/D converting means for A/D-converting the reflection light of said first and second beams detected by said photodetector;

a first memory for storing a reflection light signal of said first beam A/D-converted by said A/D converting means; and a second memory for storing a reflection light signal of said second beam A/D-converted by said A/D converting means.

12. A wire appearance inspecting apparatus as claimed in claim 9 wherein said first and second light sources are first and second semiconductor lasers; and said inspecting apparatus further comprising:
laser driving means for driving alternately said first and second semiconductor lasers every time said unit and said wire are relatively transported by a distance defined by positional resolution of said scanning mechanism.

13. A wire appearance inspecting apparatus as claimed in claim 12, further comprising:

A/D converting means for A/D-converting the reflection light of said first and second beams detected by said photodetector;

a first memory for storing a reflection light signal of said first beam A/D-converted by said A/D converting means; and a second memory for storing a reflection light signal of said second beam A/D-converted by said A/D converting means.

14. A wire appearance inspecting apparatus as claimed in claim 1 wherein said first and second light sources are arranged in such a manner that the first and second beams emitted therefrom constitute a line-symmetrical optical path.

15. A wire appearance inspecting apparatus as claimed in claim 1 wherein said wire is a bonding-wire bonded on a pad array formed on at least one edge of a semiconductor device.

16. A wire appearance inspecting apparatus as claimed in claim 15 wherein said reference position is set to such a position where said bonding-wire having the normal shape should be located.

17. A wire appearance inspecting apparatus as claimed in claim 15 wherein said reference position is set to a predetermined position on an upper horizontal plane of said semiconductor device.

18. A wire appearance inspecting apparatus as claimed in claim 15 wherein said first and second light sources are arranged in such a manner that the plane formed by said first and second beams is located in parallel to the pad array of the semiconductor device on which said wire is bonded.

19. A wire appearance inspecting apparatus as claimed in claim 1 wherein said wire height calculating means calculates the height of the wire from said reference position based on inclinations of said first and second beams and said interval.

20. A wire appearance inspecting apparatus as claimed in claim 19 wherein said wire height calculating means calculates the height $\Delta Z$ of the wire from the reference position in accordance with the following equation, wherein the inclination of said first beam relative to a vertical plane is "$\theta 1$," the inclination of said second beam relative to said vertical plane is "$\theta 2$", and said interval is $\Delta x$:

$$\Delta Z = \Delta x/(\tan \theta 1 + \tan \theta 2).$$

21. A wire appearance inspecting apparatus as claimed in claim 1, further comprising:

a means for condensing reflection light of said first and second beams from said wire to said photodetector.

22. A wire appearance inspecting apparatus as claimed in claim 1, further comprising:

an elliptical mirror in which said reference position is a first focal position, and a position where the light receiving surface of said photodetector is located in a second focal position.

23. A wire appearance inspecting apparatus as claimed in claim 1, further comprising:

means for moving said photodetector in a horizontal plane;

illuminating means for illuminating said wire; and imaging means for imaging said wire two-dimensionally.

24. A wire appearance inspecting apparatus as claimed in claim 23, further comprising:

means for moving said imaging means vertically relative to said wire.

25. A method for inspecting an appearance of a wire by using an arrangement including a first light source for emitting a first beam, a second light source for emitting a second beam which intersects with said first beam at a predetermined reference position, and a photodetector for detecting reflection light of said first and second beams, said method comprising the steps of:

detecting a first relative position between said arrangement and said wire when said first beam is reflected from said wire while relatively moving said arrangement and said wire;

detecting a second relative position between said arrangement and said wire when said second beam is reflected from said wire while relatively moving said arrangement and said wire; and calculating a height of said wire from said reference position based on an interval between said first and second relative positions.

26. A wire appearance inspecting method as claimed in claim 25 wherein said calculating step calculates the height of said wire from the reference position based on an inclination between said first and second beams, and said interval.

27. A wire appearance inspecting method as claimed in claim 25 wherein said calculating step calculates the height of $\Delta Z$ of the wire from the reference position in accordance with the following equation, wherein the inclination of said first beam relative to a vertical plane is "θ1", the inclination of said second beam relative to said vertical plane is "θ2", and said interval is $\Delta x$:

$$\Delta Z = \Delta x/(\tan \theta 1 + \tan \theta 2).$$

28. A wire appearance inspecting method as claimed in claim 25, further comprising:

a step of moving said photodetector in a horizontal plane; and a step of imaging said wire from an upper portion thereof by employing two-dimensional imaging means.

29. A wire appearance inspecting method as claimed in claim 26 further comprising:

a step of detecting a shift in said reference position based on image information obtained from said two-dimensional imaging means; and a step of moving said two-dimensional imaging means vertically to reduce said shift in the reference position.

30. A method for inspecting an appearance of a wire by using an arrangement including a first semiconductor laser for emitting a first beam, a second semiconductor laser for emitting a second beam which intersects with said first beam at a predetermined reference position, and a photodetector for detecting reflection light of said first and second beams, said method comprising the steps of:

detecting reflection light of said first beam and reflection of said second beam independently, while alternatively emitting said first and second beams from said first semiconductor laser and said second semiconductor laser and relatively moving said arrangement and said wire;

detecting a relative transport amount between said arrangement and said wire which are transported since the reflection light of the first beam from said wire is detected, and until the reflection light of the second beam from said wire is detected; and calculating a height of said wire from said reference position based on said relative transport amount.

31. A wire appearance inspecting method as claimed in claim 30 wherein said calculating step calculates the height of said wire from the reference position based on an inclination between said first and second beams, and said relative transport amount.

32. A wire appearance inspecting method as claimed in claim 30 wherein said calculating step calculates the height $\Delta Z$ of the wire from the reference position in accordance with the following equation, wherein the inclination of said first beam relative to a vertical plane is "θ1", the inclination of said second beam relative to said vertical plane is "θ2", and said relative transport amount is $\Delta x$:

$$\Delta z = \Delta x/(\tan \theta 1 + \tan \theta 2).$$

* * * * *